(12) United States Patent
Miyauchi et al.

(10) Patent No.: US 7,189,000 B2
(45) Date of Patent: Mar. 13, 2007

(54) IMAGE-QUALITY CONTROL SYSTEM

(75) Inventors: Akihiro Miyauchi, Kuroiso (JP); Yoichi Takada, Otawara (JP)

(73) Assignees: Kabushiki Kaisha Toshiba, Tokyo (JP); Toshiba Medical Systems Corporation, Otawara-Shi (JP)

( * ) Notice: Subject to any disclaimer, the term of this patent is extended or adjusted under 35 U.S.C. 154(b) by 172 days.

(21) Appl. No.: 11/014,952

(22) Filed: Dec. 20, 2004

(65) Prior Publication Data

US 2005/0157848 A1    Jul. 21, 2005

(30) Foreign Application Priority Data

Dec. 22, 2003  (JP) .............................. 2003-424771

(51) Int. Cl.
*G01D 18/00* (2006.01)

(52) U.S. Cl. ..................................... 378/207; 378/210

(58) Field of Classification Search ................ 378/207, 378/210; 382/128, 131, 132; 600/407, 411, 600/425; 700/275; 702/182, 183, 184, 185; 705/2, 3

See application file for complete search history.

(56) References Cited

U.S. PATENT DOCUMENTS

| | | | |
|---|---|---|---|
| 5,841,835 A | 11/1998 | Aufrichtig et al. | 378/207 |
| 6,115,489 A | 9/2000 | Gupta et al. | 382/141 |
| 6,272,469 B1 | 8/2001 | Koritzinsky et al. | 705/2 |
| 6,516,324 B1 | 2/2003 | Jones et al. | 707/104.1 |

FOREIGN PATENT DOCUMENTS

EP    0 874 536 A1    10/1998

*Primary Examiner*—Courtney Thomas
(74) *Attorney, Agent, or Firm*—Oblon, Spivak, McClelland, Maier & Neustadt, P.C.

(57) ABSTRACT

An image-quality control system including a terminal connected to medical diagnostic imaging apparatus and a service center system for transmitting a maintenance report of the medical diagnostic imaging apparatus to the terminal. The terminal includes a first receiving unit for receiving a report transmitted from the service center system and a first transmitting unit for transmitting an image or image-quality parameters of the image. The service center system includes a second receiving unit for receiving the image or image-quality parameters from the terminal, an image-quality parameter database for storing the image-quality parameters, a determination section for determining if the stored image-quality parameters correspond with specified reference values, a report generating section for generating a report including the determination of the image-quality parameters, and a second transmitting unit for transmitting the generated report.

12 Claims, 14 Drawing Sheets

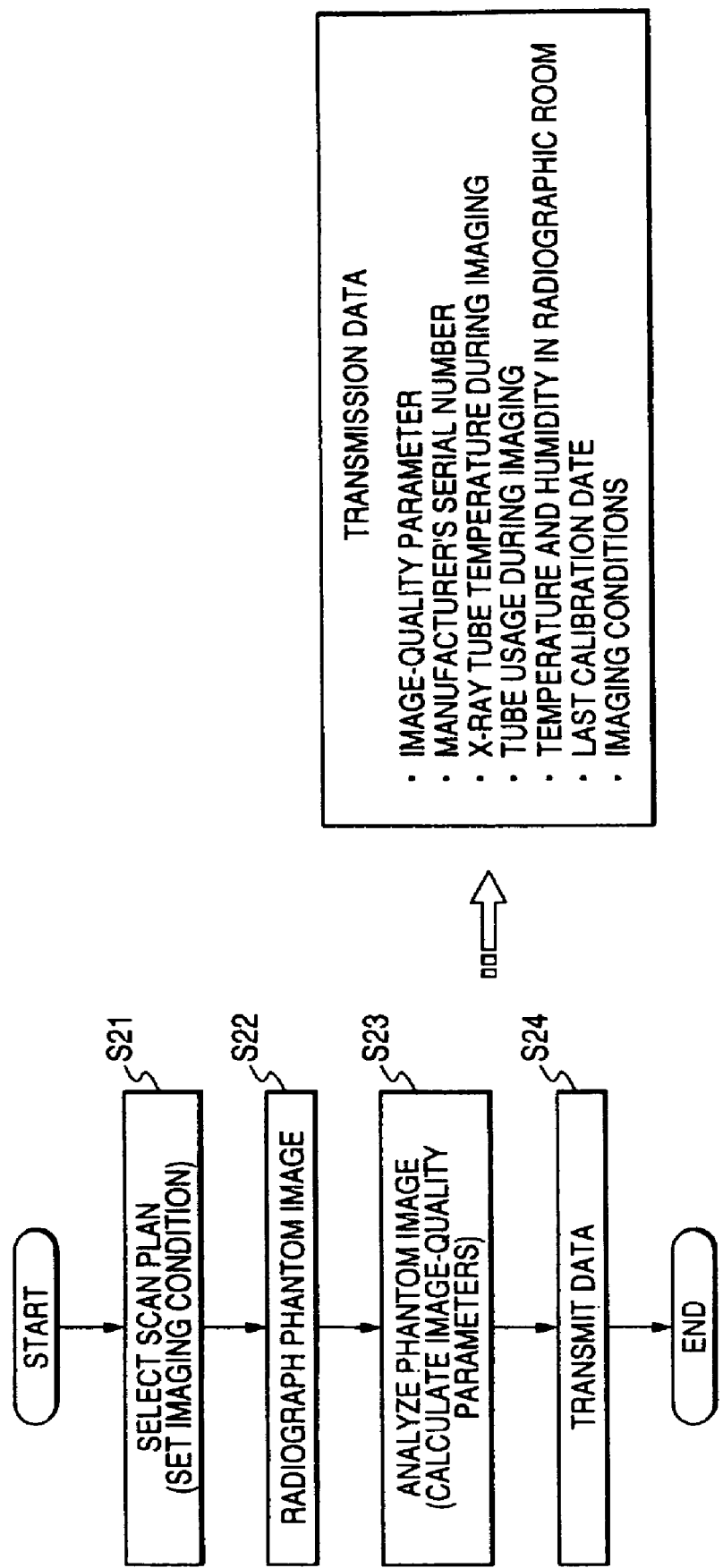

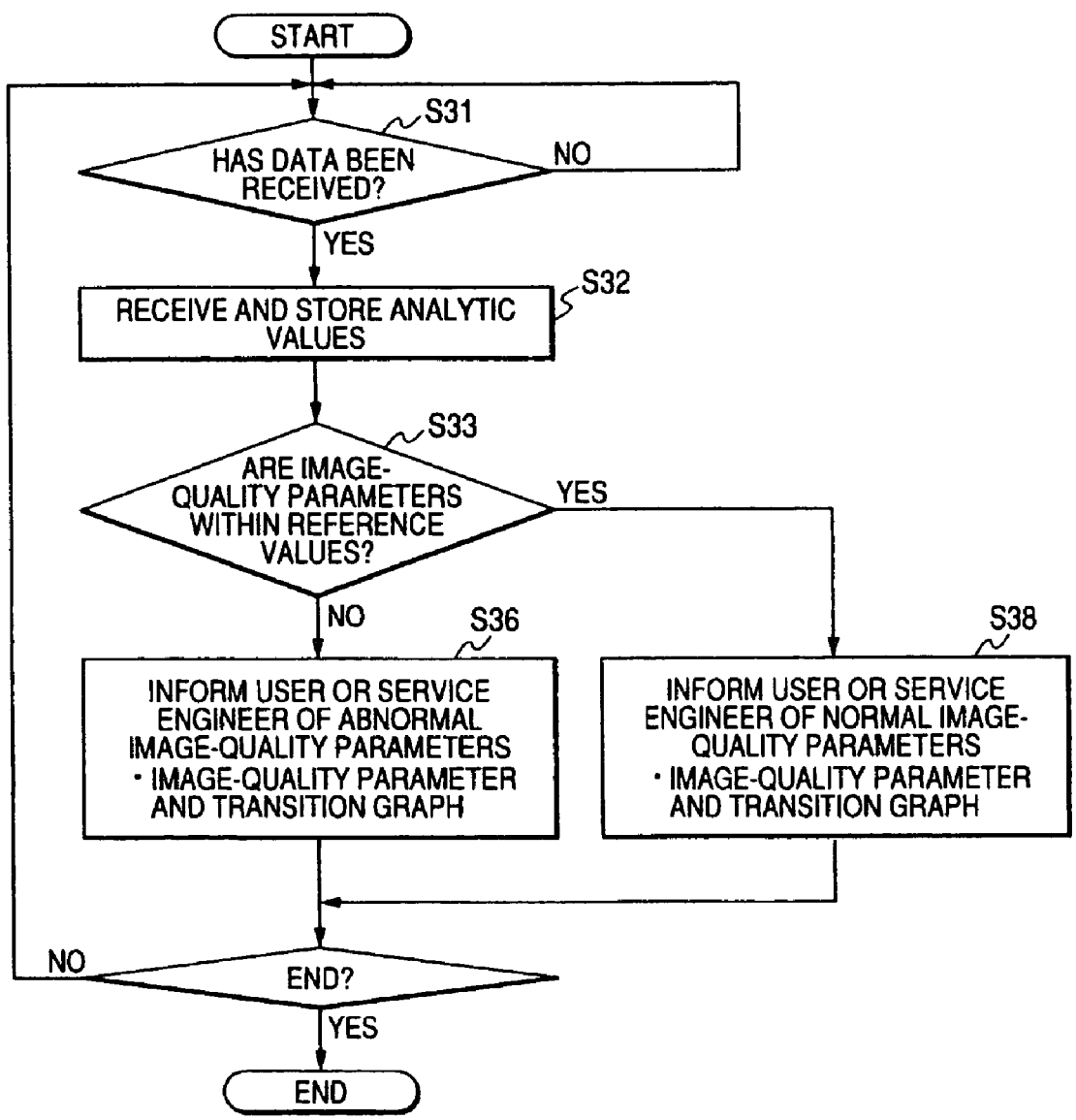

FIG. 4

QUALITY CONTROL DB

| MANUFACTURER'S SERIAL NUMBER | TYPE | IMAGING DATE | MANAGEMENT | IMAGE-QUALITY PARAMETER ||| IMAGING CONDITIONS ||| STATE OF TUBE || AIR CONDITION ||
|---|---|---|---|---|---|---|---|---|---|---|---|---|---|
| | | | | RESOLUTION | CONTRAST | LINEARITY | TUBE CURRENT | TUBE VOLTAGE | IMAGING TIME | X-RAY TUBE TEMPERATURE | TUBE USAGE | TEMPERATURE | HUMIDITY |
| XR1234 | XR_A | 2000/1/1 | PERIODICALLY | xxx.x | xx.x | xxxx | aaa | bbbbb | ttt | sss | ppp | ff.f | hh |
| CT2345 | CT_A | 2000/3/4 | SHIPMENT | | | | | | | | | | |
| CT2346 | CT_B | 2000/4/5 | SHIPMENT | | | | | | | | | | |
| CT2345 | CT_A | 2000/4/6 | INSTALLATION | | | | | | | | | | |
| XR1234 | XR_A | 2000/4/7 | MAINTENANCE | | | | | | | | | | |
| CT2345 | CT_A | 2000/5/4 | PERIODIC | | | | | | | | | | |
| | | | | | | | | | | | | | |
| | | | | | | | | | | | | | |

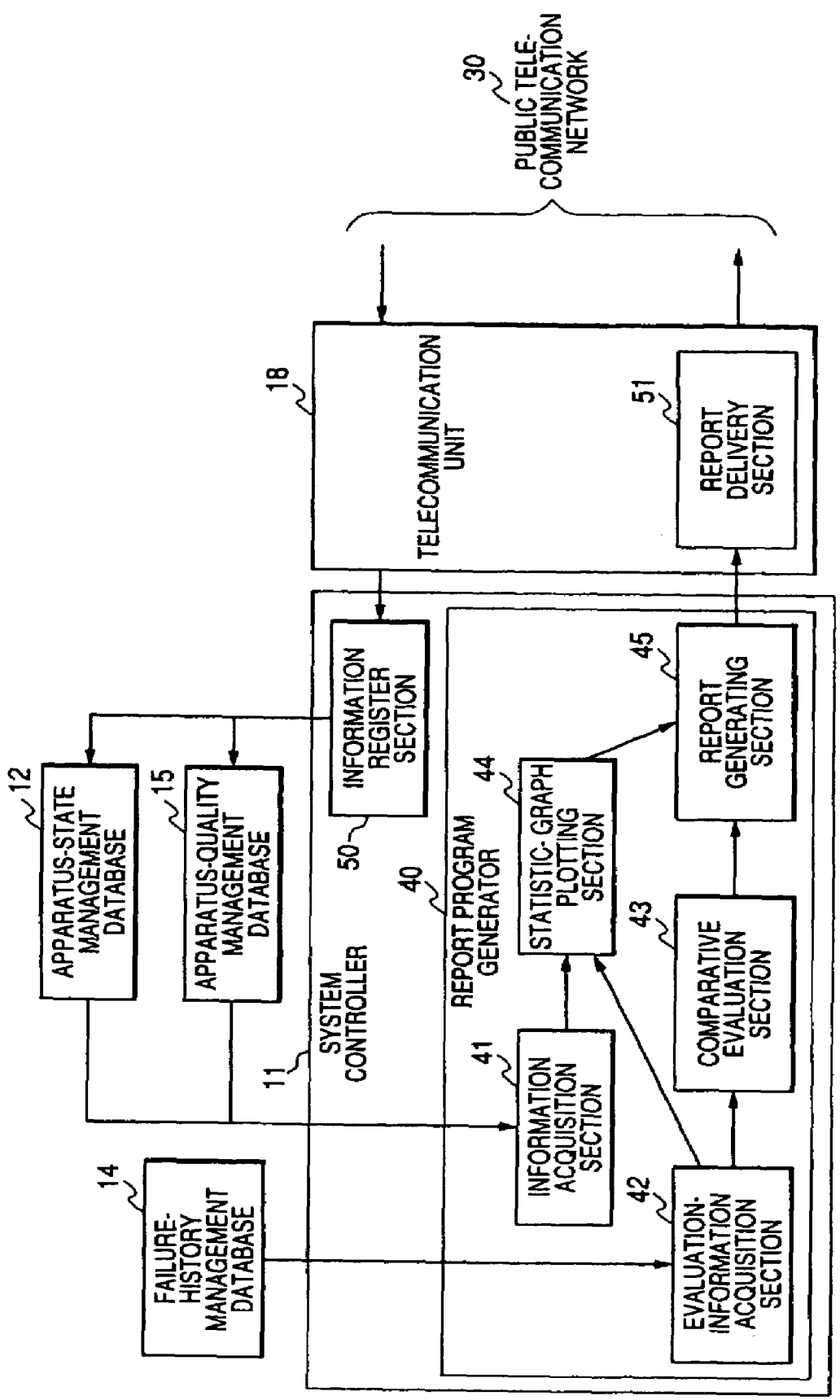

FIG. 6

RELIABILITY REPORT

| Hospital Name: | **** Hospital | | Model: | ****** |
|---|---|---|---|---|
| Modality: | CT | | Reporting Date: | 10/01/2002 18:47:39 |
| SystemID: | SYS_0W_001 | | Report No: | 2739 |
| Reporting Term: | From: 09/01/2003 To: 09/30/2003 | | | |

1. Planned Maintenance/General - Repair History

| DATE | TYPE | Description |
|---|---|---|
| · 09/01/2003 | General Repair | Detector problem |
| · 09/10/2003 | General Repair | FLICKER/FLASH ERROR DOWN ASK FOR CHRISTA |
| · 09/12/2003 | General Repair | abnormal XC errors. resetting system hard shutdown./ar |
| · 09/13/2003 | General Repair | FILES NOT TRANSFERING SINCE SCANNER CAME BACK UP. |
| · 09/14/2003 | General Repair | after doing a head scan. Then a knocking sound after angling the gantry. |
| · 09/16/2003 | Planned Maintenance | Scheduled PM. SLIP RING INSPECTION |
| · 09/16/2003 | General Repair | BROKEN HEAD REST |
| ...... | General Repair | Kc errors and overcurrent errors-also got |
| ...... | | |

FIG. 9

| 3. Calibration information for Image quality | |
|---|---|
| DATE | CALIBRATION TYPE |
| 09/04/2003 | Warmup-Air-Calibration |
| 09/05/2003 | Warmup-Air-Calibration |
| 09/06/2003 | Warmup-Air-Calibration |
| 09/08/2003 | Warmup-Air-Calibration |
| 09/09/2003 | Warmup-Air-Calibration |
| 09/09/2003 | Warmup-Air-Calibration |
| 09/11/2003 | Warmup-Air-Calibration |
| 09/11/2003 | Warmup-Air-Calibration |
| 09/12/2003 | Warmup-Air-Calibration |
| 09/13/2003 | Warmup-Air-Calibration |
| 09/14/2003 | Warmup-Air-Calibration |
| 09/15/2003 | Warmup-Air-Calibration |
| 09/15/2003 | Warmup-Air-Calibration |
| 09/16/2003 | Warmup-Air-Calibration |
| 09/17/2003 | Warmup-Air-Calibration |
| 09/18/2003 | Warmup-Air-Calibration |
| 09/18/2003 | Warmup-Air-Calibration |
| 09/20/2003 | Warmup-Air-Calibration |
| 09/21/2003 | Warmup-Air-Calibration |
| 09/21/2003 | Warmup-Air-Calibration |
| 09/22/2003 | Warmup-Air-Calibration |
| 09/24/2003 | Warmup-Air-Calibration |
| 09/26/2003 | Warmup-Air-Calibration |
| 09/27/2003 | Warmup-Air-Calibration |
| 09/28/2003 | Warmup-Air-Calibration |
| 09/28/2003 | Warmup-Air-Calibration |
| 09/29/2003 | Warmup-Air-Calibration |

FIG. 10

3. CALIBRATION AND WARM-UPS (FULL DETAIL)

WARM-UPS STATUS

| SUNDAY | MONDAY | TUESDAY | WEDNESDAY | THURSDAY | FRIDAY | SATURDAY |
|---|---|---|---|---|---|---|
| - | - | - | - | - | - | 1 |
| 2 | 3 | 4 | 5 | 6 | 7 | 8 |
| 9 | 10 | 11 | 12 | 13 | 14 | 15 |
| 16 | 17 | 18 | 19 | 20 | 21 | 22 |
| 23 | 24 | 25 | 26 | 27 | 28 | 29 |
| 30 | - | - | - | - | - | - |

▨ : PERFORMED   YELLOW: SYSTEM USED   WITH IN 3 MONTH   WITH IN 6 MONTH

AIR & WATER CALIBRATION STATUS

FIG. 11
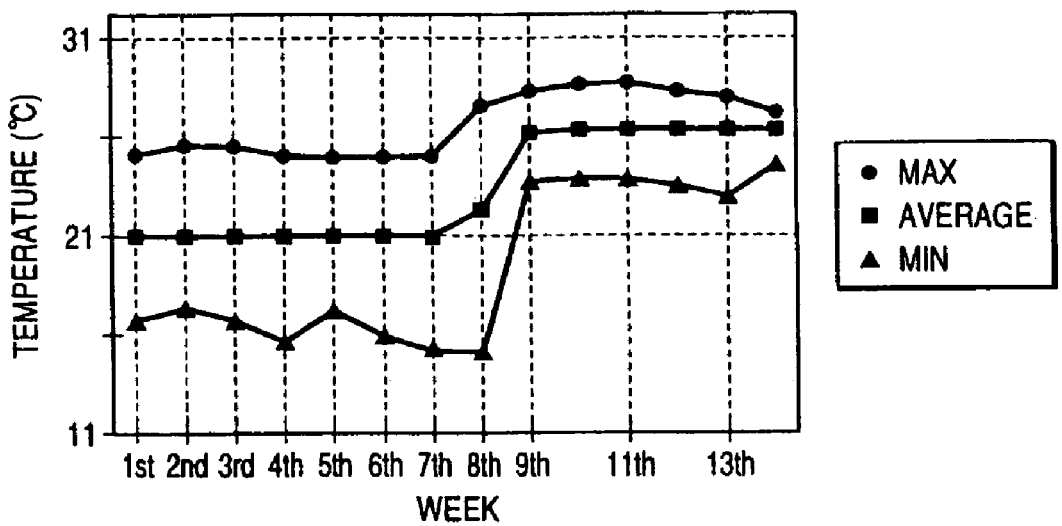
0°C < X
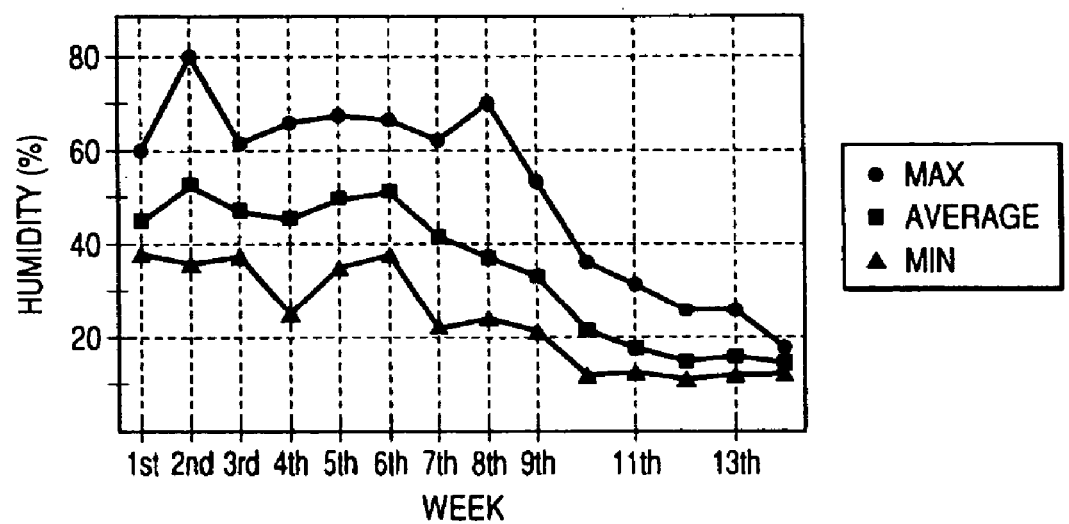

IMAGE-QUALITY CONTROL SYSTEM

BACKGROUND OF THE INVENTION

1. Field of the Invention

The present invention relates to a performance determination of medical imaging equipment installed in medical institutions such as hospitals and, more particularly, it relates to an image-quality control system for evaluating and determining the quality of medical images.

2. Description of the Related Art

Hitherto, when the image quality of medical imaging equipment installed in medical institutions is evaluated quantitatively by the request from the user of the equipment, service companies of the equipment took phantoms to the installation site and collected the scanned-image data of the phantoms. The collected data was read (the contents of the images were observed) by experts in reading images and then the difference between the data and reference data was evaluated. The image quality was evaluated depending on whether or not it is within predetermined reference values presented in specifications for each type of medical imaging equipment.

On the other hand, the image quality of medical imaging equipment installed in medical institutions is often evaluated quantitatively by reading the data of scanned images of evaluation phantoms that servicemen took to the institutions into computers having analysis software and analyzing it.

When the result of the analysis is beyond the range of the reference values, remedies that are presented in manuals etc. by analysis item are carried out to maintain the standard of image quality.

The image quality characteristics of medical imaging equipment are very complicated and vary delicately. This is because medical images are reconstructed under the influence of the characteristics of many components and complicated processes until image generation and then outputted. Accordingly, in order to check the components to find the cause of the defect in image quality, it takes a lot of time to replace the components by trial and error and to validate it, so that medical imaging examination and diagnosis must be stopped for a long time. Furthermore, it was also disadvantageous that image quality depends on the technical capability of servicemen depending on their experience.

SUMMARY OF THE INVENTION

The present invention has been made in consideration of the problems of the conventional systems. Accordingly, it is an object of the invention to provide an image-quality control system for recognizing degradation in image quality in an early state by comparing image-quality evaluation data acquired by using a phantom with a database in which the operating state of medical imaging equipment is stored continuously and a failure-cause analysis database and giving an instruction of remedies for finding the cause of the degradation in image quality in a short time.

In order to solve the foregoing problems, there is provided an image-quality control system which includes a terminal connected to medical diagnostic imaging apparatus and a service center system configured to transmit a maintenance report of the medical diagnostic imaging apparatus to the terminal via a network. The terminal includes a first receiving unit configured to receive a report transmitted from a second transmitting unit of the service center system and a first transmitting unit configured to transmit an image imaged by the medical diagnostic imaging apparatus or image-quality parameters of the image via the network. The service center system includes a second receiving unit configured to receive the image or image-quality parameters transmitted from the first transmitting unit of the terminal, an image-quality parameter database configured to store the image-quality parameters of the medical diagnostic imaging apparatus from the image or the image-quality parameters received by the second receiving unit, a determination section configured to determine whether or not the image-quality parameters stored in the image-quality parameter database lie within specified reference values, a report generating section configured to generate a report including the determination of the image-quality parameters by the determination section, and a second transmitting unit configured to transmit the report including the determination of the image-quality parameters generated by the report generating section to the first receiving unit of the terminal via the network.

Preferably, the image-quality parameters include resolution, contrast, and linearity.

Preferably, the medical diagnostic imaging apparatus is an X-ray CT scanner; and the report generating section generates a report on CT linearity, low contrast, spatial resolution (MTF), noise, slice thickness, and uniformity of a desired phantom, as image-quality parameter information.

Preferably, the service center system further includes an environment information database storing environment information of the medical diagnostic imaging apparatus collected via the network; and the report generating section generates a report including the determination for the image-quality parameters and the environment information. Preferably, the service center system further includes an apparatus-operation information database storing operating information of the medical diagnostic imaging apparatus collected via the network; and the report generating section generates a report including the determination for the image-quality parameters and information on the calibration of the medical diagnostic imaging apparatus.

Preferably, the service center system further includes an apparatus-operation information database storing operating information of the medical diagnostic imaging apparatus collected via the network; and the report generating section generates a report of information on the latest calibration stored in the apparatus-operation information database, the temperature and humidity of the exposure room, and tube usage, in addition to CT linearity, low contrast, spatial resolution (MTF), noise, slice thickness, and uniformity of a desired phantom.

Preferably, the information on the latest calibration includes tube voltage and tube current to an X-ray tube, scanning time, the date and time of collecting combinations of FOVs, and wherein the information on tube usage includes X-ray-tube exposure time and rotation count.

Preferably, the report generating section displays a comparison of the latest information and the past information to allow recognition of changes in the image-quality parameters with time.

When the image-quality parameters are determined to be beyond the range of reference values, preferably, the determination section analyzes whether or not the determination that the image-quality parameters are beyond the range of the reference values is caused by the environment of the exposure room or by the trouble of parts and specifies a failure part by determining the normal/abnormal of at least one of the environment information of the exposure room and calibration information stored in the apparatus-operation information database.

Preferably, the image-quality parameters are image-quality parameters when the medical diagnostic imaging apparatus imaged a phantom.

When it is determined by the determination section that the image-quality parameters are beyond the range of the reference values, preferably, the second transmitting unit transmits the effect to at least one of the terminal, the medical diagnostic imaging apparatus, and a terminal owned by a service engineer.

When it is determined by the determination section that the image-quality parameters are beyond the range of the reference values, preferably, at least one of a failure analyzing procedure for the medical diagnostic imaging apparatus, replacement parts for recovering the failure, and a recovery procedure for recovering the failure is determined from the determination.

The system and method for controlling image-quality performance according to the present invention have an advantage in that degradation in image quality can be recovered in a short time by searching a failure-cause analysis database for the cause of the degradation in image quality. The system also has the advantage of preventing degradation in image quality by grasping changes in the state of the apparatus and environment which lead to the degradation in image quality, since it monitors the operating state of medical imaging equipment. The system also has the advantage of recovering degradation in image quality in a shorted time, since operating conditions of the equipment and environmental conditions, which may cause degradation in image quality, can be changed by the users themselves, such as doctors and inspecting engineers, by executing a predetermined scan plan by the users.

BRIEF DESCRIPTION OF THE DRAWINGS

FIG. 2 is a flowchart for acquiring image-quality check data according to the first embodiment;

FIG. 3 is a main flowchart of the first embodiment;

FIG. 4 is a data table showing an example of the structure of an apparatus-quality management database recorded in the first embodiment;

FIG. 5 is a block diagram showing the outline of a data flow according to the first embodiment;

FIG. 6 is a table of an example of a medical-equipment maintenance history in a report according to the first embodiment;

FIG. 9 is a table of an example of a calibration acquisition history in a report according to the second embodiment;

FIG. 10 is a table of another example of the calibration acquisition history in the report according to the second embodiment;

FIG. 11 is a graph of an example of temperature history and humidity history in apparatus operating environment in the report according to the second embodiment;

DESCRIPTION OF THE PREFERRED EMBODIMENTS (First Embodiment)

An image-quality control system according to a first embodiment of the present invention will be described hereinbelow with reference to the drawings.

Figure 1:
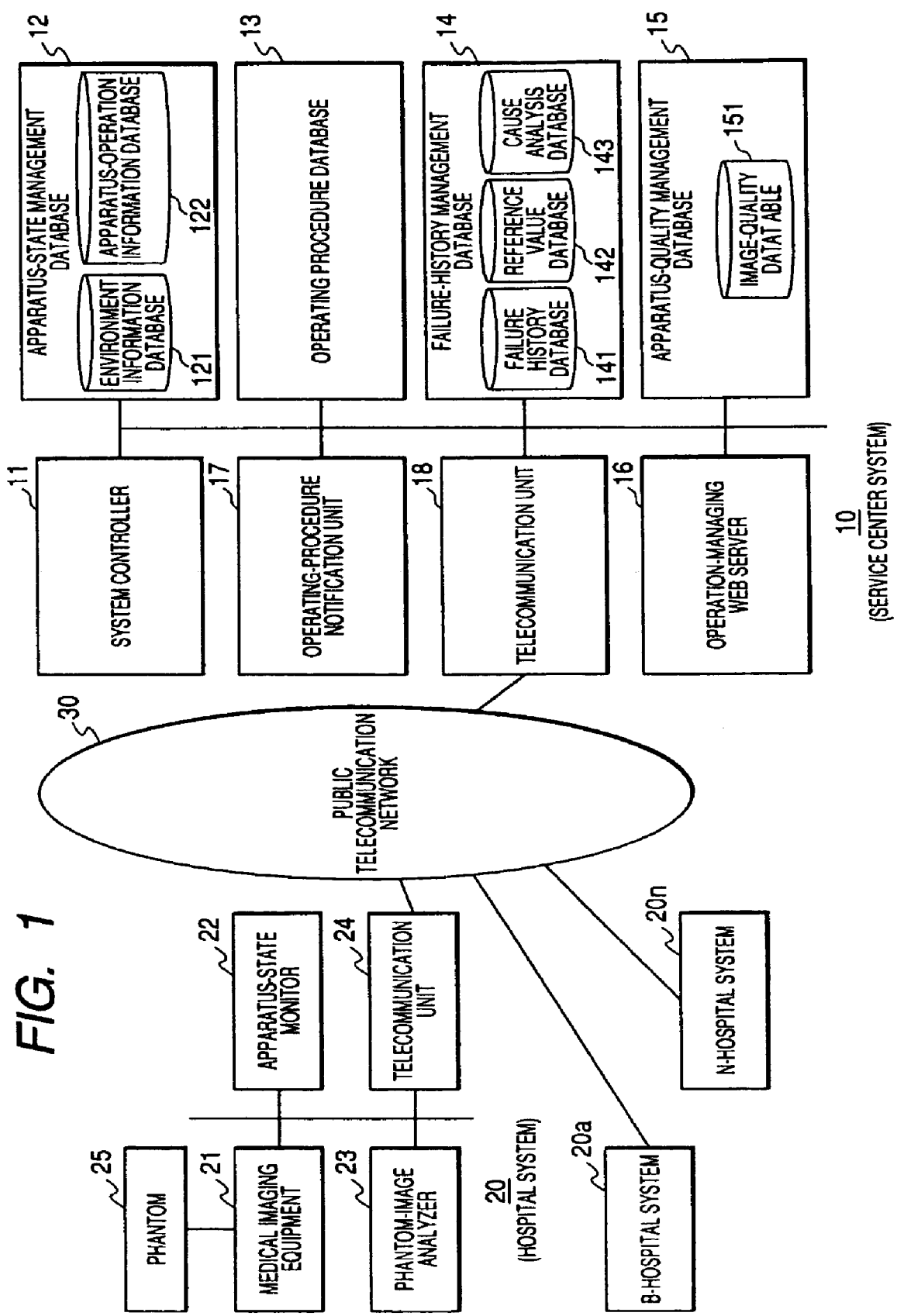
FIG. 1 is a block diagram showing the structure of a first embodiment of the present invention.

FIG. 1 is a block diagram of the first embodiment of the invention.

As shown in FIG. 1, the image-quality control system according to this embodiment includes a public telecommunication network 30, a service center system 10 connected thereto, a hospital system 20, and other hospital systems 20a to 20n.

The service center system 10 includes a system controller 11, an apparatus-state management database 12, an operating procedure database 13, a failure-history management database 14, an apparatus-quality management database 15, an operation-management Web server 16, an operating-procedure notification unit 17, and a telecommunication unit 18 connected to the public telecommunication network 30, which are individually connected via a network.

The hospital system 20 is installed in a hospital and includes medical imaging equipment 21 as an object of image-quality control, an apparatus-state monitor 22 connected thereto via a network, a phantom-image analyzer 23, a telecommunication unit 24 connected to the public telecommunication network 30, and a phantom 25 having an imitation object for use in collecting image-quality evaluation data.

Furthermore, the hospital systems 20a to 20n of medical imaging equipment, which are similar in construction to the hospital system 20, installed in other hospitals, to be the objects of image-quality control, connect to the public telecommunication network 30.

The service center system 10 will be described in detail.

The apparatus-state management database 12 includes an environment information database 121 that stores a data table of environment data of medical imaging equipment of hospitals, which are to be the object of image-quality control, that is environmental temperature, humidity, etc. of the apparatus installation site, for each of the apparatus identification codes; and an apparatus-operation information database 122 that stores a data table of operating-state data such as a X-ray tube temperature, a total tube operating time, and the date and time of the observation or acquisition thereof. The operating-state data of the medical imaging equipment for each apparatus identification code is acquired and outputted by the apparatus-state monitor 22 of the object hospital system 20 and then transferred to the service center system 10 via the public telecommunication network 30.

The operating procedure database 13 stores data for recovery such as elimination of the cause of degradation in image quality or readjustment with reference to analysis data, more specifically, it stores an operating procedure table of information or data such as document numbers and their data page of the operation manual and a replacement part number.

The failure-history management database 14 includes a failure history database 141 that stores a data table of failure-occurrence date, quality problems such as failure and image-quality degradation, and the numbers of parts including revisions after remedies such as replacement for each of apparatus identification codes of medical imaging equipment in failure remedy service or maintenance service. The failure-history management database 14 also includes a reference value database 142 and a cause analysis database 143. The reference value database 142 stores a data table of setting conditions for image-quality parameters, calibration, and air conditioning, which are assumed from extraction results of image-quality-related data in the failure history database 141 and setting standard at the time of designing the apparatus. The cause analysis database 143 stores a data table of cause-finding information such as a cause analysis technique and tracking procedure for each of failures or degradations in image quality which are categorized hierarchically. The reference values in the reference value database 142 are sometimes set by clinical fields, such as an internal department, an external department, and a neurosurgery department or body parts, such as circulatory organs, digestive organs, head, breast, and abdominal regions, for which medical imaging equipment is used.

The apparatus-quality management database 15 stores an image-quality data table 151 in which image-quality data as a result of a performance test immediately before factory shipment, image-quality data as a result of installation check after installation in the hospital, and image-quality data as a result of a regular performance test or a test at the occurrence of failure are recorded in addition to their execution date and time data, imaging conditions, and environmental conditions.

The telecommunication unit 24 of the hospital system 20 of this embodiment serves as a terminal including a first receiving unit and a first transmitting unit of the invention. Similarly, the telecommunication unit 18 of the service center system 10 according to the embodiment serves as a second receiving unit and a second transmitting unit of the invention. The apparatus-quality management database 15 according to the embodiment serves as an image parameter database of the invention.

The operation of the embodiment with the foregoing structure will now be described.

In a hospital including the medical imaging equipment 21 shown in FIG. 1, the apparatus-state monitor 22 of the hospital system 20 collects data for the apparatus-state management database 12, such as use environment data, namely, the temperature and humidity in the installation room and tube temperature, supply-voltage-variation continuous measurement data of an equipment driving source, and operation data. More specifically, for X-ray CT scanners, the apparatus-state monitor 22 collects tube current, tube voltage, and tube-use-frequency measurement data indicated by the number of exposures or scanning time. The collected data is summarized by maximum- and minimum-value extraction, reference range determination, and accumulation, and whose singularity is extracted and temporarily stored in the apparatus-state monitor 22 as a day-to-day data file.

The data for the apparatus-state management database 12 is collected repeatedly at predetermined time intervals until the completion of operation of the medical imaging equipment 21 is sensed. The use environment data and the operation data of the day are totaled generally at midnight and transferred to the apparatus-state management database 12 of the service center system 10 via the telecommunication units 24 and 18 through the public telecommunication network 30. After the daily data transfer, waiting stored (use) environment data is measured continuously during power supply to the object apparatus. Similarly, daily summation of the operating time, the X-ray exposure time, and a total rotation number of the gantry are determined and recorded in the apparatus-state management database 12 generally at midnight.

On the other hand, the apparatus-state monitor 22 acquires and transmits quality evaluation data by the image-quality-check data acquisition procedure of FIG. 2. In the flowchart of FIG. 2, on the day of regular execution of image-quality check, e.g., every day or every week, in step S21, a specified scan plan for checking image-quality performance is selected for the phantom 25 disposed in the hospital by the service center system 10 as the imaging object. The disposed phantom 25 is an anthropogenic object for acquiring specific image-quality evaluation data, e.g., (1) which has a multilayer structure to determine slice thickness, (2) which includes tiny iron balls embedded to determine the resolution, and (3) which includes isometric wires in four directions to obtain accurate distance. Imaging conditions for image-quality check data of the medical imaging equipment 21 include the width of the layers of the phantom 25 set to scanning stroke and conditions of tube voltage and tube current appropriate to the clinical fields to which medical imaging equipment 21 is applied, such as object clinical regions of an internal department, an external department, and a neurosurgery department. The conditions are set to specified scan plan or either of them is designated to acquire data.

In step S22, the phantom 25 is imaged by the medical imaging equipment 21 to acquire phantom image data that is image-quality check data.

In step S23, the acquired image check data is read by the phantom-image analyzer 23 of the hospital system 20, where the contents of the image data are analyzed. More specifically, the read phantom image data is recognized as a position of a marker embedded in the phantom 25 on a digital image and analyzed quantitatively using various algorisms by the data analysis software installed in the phantom-image analyzer 23. Thus, index values for evaluating the image quality of medical imaging equipment are analyzed; for X-ray CT scanners, e.g., the contents of image data in the image-quality related items such as slice thickness, CT linearity, and spatial resolution. Other medical imaging equipment, such as ultrasonic devices and MRI machines, analyzes index values such as distance measurement accuracy, display linearity accuracy, and resolution accuracy.

In step S24, the image-quality parameters, or the analysis of the phantom-image analyzer 23, are transmitted together with the analysis date and the apparatus identification code of the medical imaging equipment 21 by the telecommunication unit 24 to the service center system 10 via the public telecommunication network 30 through the telecommunication unit 18.

The received analysis is stored additionally in the image-quality data table 151 by apparatus identification code, in which previous image-quality evaluation data in the apparatus-quality management database 15 is stored. The transmitted data is compared with the past data and criterion, according to the image-quality evaluation program in the system controller 11, where it is determined whether the image quality of the medical imaging equipment 21 that has transmitted the data maintains a specified standard or in degradation that needs maintenance.

Then the flow of the image-quality control system of the system controller 11 on the service-system center side according to the first embodiment will be described.

FIG. 3 is a main flowchart of the image-quality control system according to the first embodiment, in which image-quality check data is transmitted and the image-quality performance of the object medical imaging apparatus is controlled.

When image-quality check data is acquired by using the phantom 25, shown in the flowchart of FIG. 2, on the day of regular execution of image-quality check that the user has requested in advance, e.g., every day or every week, image-quality parameters, apparatus-state data, etc. are transmitted together with apparatus identification data in step S24. In step S31 of the system flowchart of this embodiment, the data transmitted from the medical imaging equipment installed in local hospitals is received.

In step S32, as soon as the data is received, analysis data such as the image-quality parameters is stored in the apparatus-quality management database 15. As shown in FIG. 4, the image-quality data table 151 in the apparatus-quality management database 15 is a list of manufacturer's serial numbers, machine types, data acquisition dates, and data acquisition objects, image-quality parameters such as resolution, contrast, linearity, imaging conditions such as tube current, tube voltage, and imaging time, the state of a tube such as tube temperature and tube usage, and environment and air condition such as room temperature and room humidity.

In step S33, it is determined whether or not the data of the image-quality parameters recorded in step S32 is within the reference values set and recorded in the reference value database 142 by machine type.

When it is determined in step S33 that the transmitted and recorded image-quality parameters are within the reference values, the program proceeds to step S38, wherein a mail indicative of the fact that the image-quality performance of the medical imaging equipment 21 is normal and the data are transmitted to the manager of the medical imaging equipment 21 of the medical institution. Also, an instruction to display a message to the same effect at the next activation of the medical imaging equipment is given to the medical imaging equipment 21 via the telecommunication units 18 and 24 through the public telecommunication network 30 to inform the user of the medical imaging equipment 21 of the fact that the equipment 21 is in normal operation. Also a report that the image-quality performance of the medical imaging equipment is normal is given to a service engineer who maintains the medical imaging equipment 21 or a service station in charge.

On the other hand, when it is determined in step S33 that the transmitted and recorded image-quality parameters are beyond the reference values, the program proceeds to step S36, wherein a mail indicative of the fact that trouble has occurred in the image-quality performance of the medical imaging equipment 21 and so the medical imaging equipment 21 is in failure is transmitted to the manager of the medical imaging equipment 21 of the medical institution. Also, an instruction to display a message to the same effect and that the medical imaging equipment 21 is unavailable and so an appropriate remedy is needed at the next activation of the medical imaging equipment 21 is given to the medical imaging equipment 21 via the telecommunication units 18 and 24 through the public telecommunication network 30 to inform the user of the medical imaging equipment 21 of the fact that the equipment 21 is unavailable.

The foregoing process is executed by a report program generator 40 installed in the system controller 11 under the control of a CPU (not shown) of the system controller 11. FIG. 5 shows the outline of a data flow of this process. The report program generator 40 includes an information acquisition section 41, an evaluation-information acquisition section 42, a comparative evaluation section 43, a statistic-graph plotting section 44, and a report generating section 45.

Various information transmitted from the hospital system 20 via the public telecommunication network 30 to the telecommunication unit 18 is first sent to an information register section 50 of the system controller 11. The information register section 50 classifies the received information by type of information into predetermined databases. For example, information on quantitative values of an image is transmitted to the apparatus-quality management database 15, while environmental information and operating information of the apparatus are transmitted to the apparatus-state management database 12 and stored therein.

Upon reception of the information, the information acquisition section 41 calls up information on the quantitative values of the image from the apparatus-quality management database 15 and the environmental information and operating information of the apparatus from the apparatus-state management database 12 to acquire them. At the same time, the evaluation-information acquisition section 42 calls up image-quality parameters (reference image-quality parameters) serving as criteria from the reference value database 142 in the failure-history management database 14.

The comparative evaluation section 43 compares the information on the image quantitative values and equipment environmental information and operating information with the reference image-quality parameters to perform the determination in step S33 of FIG. 3.

The determination is sent to the report generating section 45 together with a graph and a table of the items which are produced from the information by the statistic-graph plotting section 44 and summarized to a report in a specified format. The report is converted to a desired data format by a report delivery section 51 in the telecommunication unit 18 and then sent to the hospital system 20 via the public telecommunication network 30.

Figure 7:
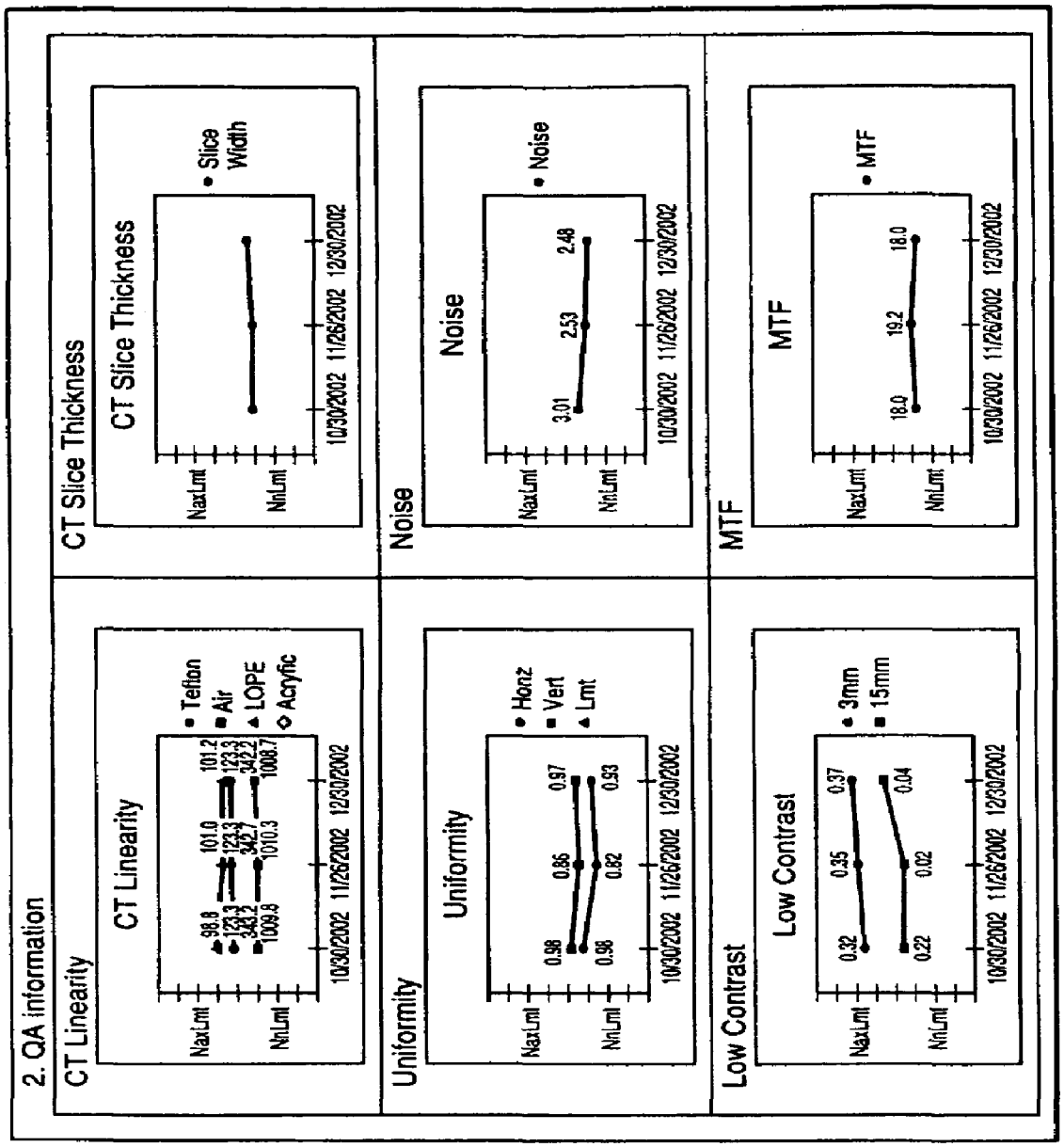
FIG. 7 is a diagram of an example of a quantitative image quality analysis in the report according to the first embodiment.

Examples of the report are shown in FIGS. 6 and 7. FIG. 6 shows a maintenance history of the medical imaging equipment 21, which is shown at the head of the report. The maintenance history of the medical imaging equipment 21 also serves as a summary of the report.

FIG. 7 shows quantitative analyses of image quality. In this example, an X-ray CT scanner is taken as medical imaging equipment, in which quantitative values of CT linearity, slice thickness, uniformity, noise, low contrast, and spatial resolution (modulation transfer function (MTF)) are graphed. When the quantitative values are within the reference values of the reference image-quality parameters, the process of step S38 in FIG. 3 is executed; when they are beyond the reference values of the reference image-quality parameters, the process of step S36 in FIG. 3 is executed.

(Second Embodiment)

Figure 8:
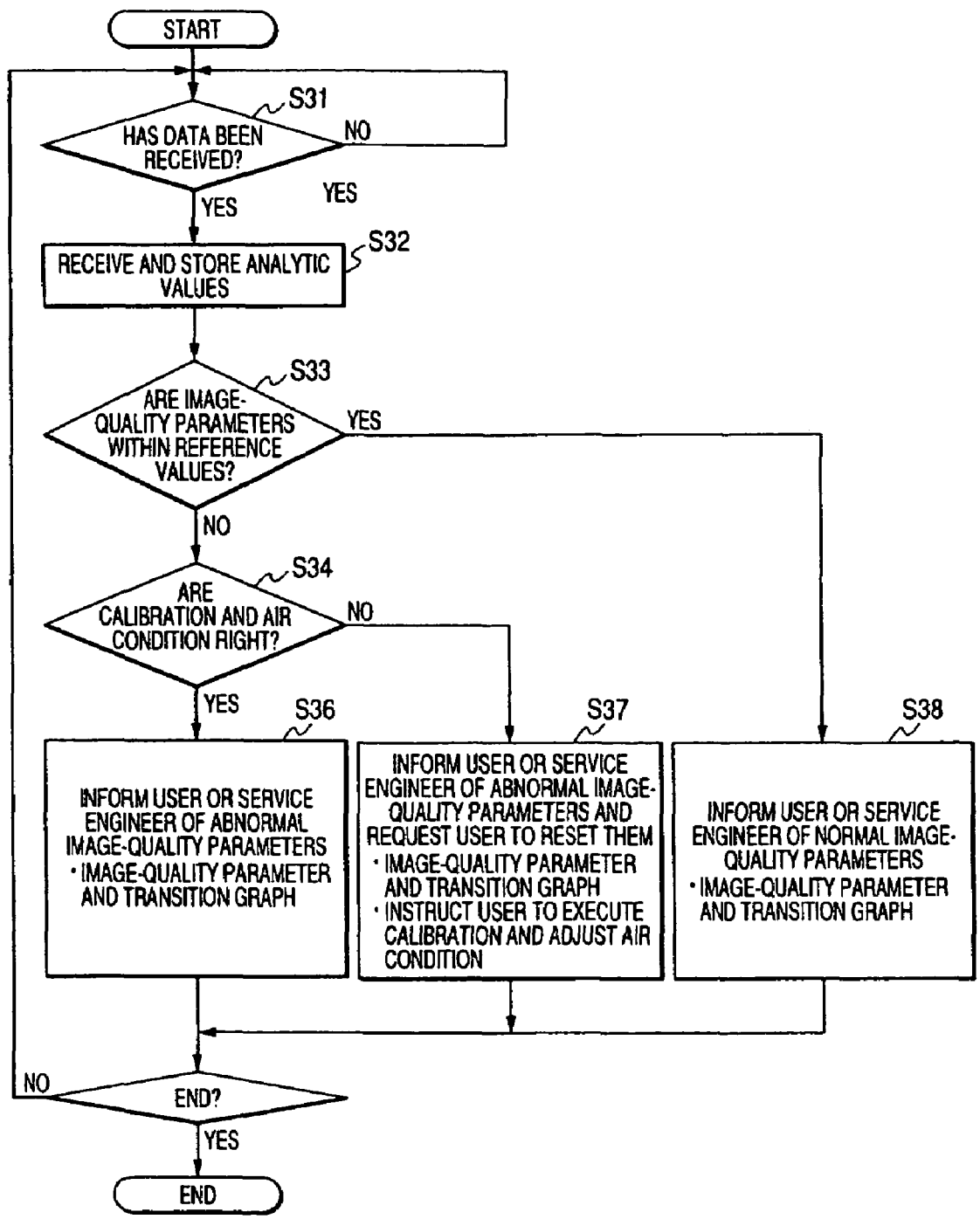
FIG. 8 is a main flowchart of a second embodiment of the invention.

An image-quality control system according to a second embodiment of the present invention will be described hereinbelow with reference to the drawings. As shown in FIG. 8, the image-quality control system of the second embodiment essentially differs from the first embodiment in that, in the flow of the image-quality control system, step S33 of determining whether or not the data of the image-quality parameters is within the image-quality-parameter reference values is followed by step S34, and the other structures and operations are substantially the same as the first embodiment and so their description will be omitted here, with the same reference numerals being given.

In this embodiment, when it is determined in step S33 that the transmitted and recorded image-quality parameters are beyond the reference values, the program proceeds to step S34, wherein it is determined whether or not record data or designated items on the calibration and air condition in the transmitted and recorded apparatus-state data differ from correct set values with reference to correct set reference-value data on the calibration and air condition from the reference value database 142 of the relevant apparatus.

When it is determined in step S34 that the setting of the calibration and air condition is not correct, the process proceeds to step S37, wherein a mail indicative of the fact that the setting of the calibration and air condition of the medical imaging equipment 21 is not correct and so the image-quality performance is decreased and that the setting of the calibration and air condition must be reset to the correct set reference-value is transmitted to the manager of the medical imaging equipment 21 of the medical institution. Alternatively, an instruction to display a message to the same effect, a calibration method for the medical imaging equipment 21, and reference adjustment instruction data on the air conditioner at the installation location at the next activation of the medical imaging equipment 21 is given to the medical imaging equipment 21 via the telecommunication units 18 and 24 through the public telecommunication network 30 to inform the user of the medical imaging equipment 21 of the fact that the equipment 21 operates incorrectly.

On the other hand, when it is determined in step S34 that the setting of the calibration and air condition is correct, the process proceeds to step S36, wherein a mail indicative of the fact that trouble occurs in the image-quality performance of the medical imaging equipment 21 and that the equipment is in failure is transmitted to the manager of the medical imaging equipment 21 of the medical institution. Alternatively, an instruction to display a message to the same effect and that the medical imaging equipment is unavailable and so an appropriate remedy is needed at the next activation of the medical imaging equipment is given to the medical imaging equipment 21 via the telecommunication units 18 and 24 through the public telecommunication network 30 to inform the user of the medical imaging equipment 21 of the fact that the equipment 21 is unavailable.

FIGS. 9 and 10 show examples of the report of a calibration collection history executed to maintain the image quality in step S34. The collection history is displayed in tabular format in FIG. 9, while it is displayed in the form of monthly calendar in FIG. 10.

FIG. 11 shows examples of a temperature history and a humidity history in apparatus operating environments, in which the highest temperature (humidity) and the lowest temperature (humidity) are graphed in addition to average temperature (humidity) for a prescribed period.

Figure 12:
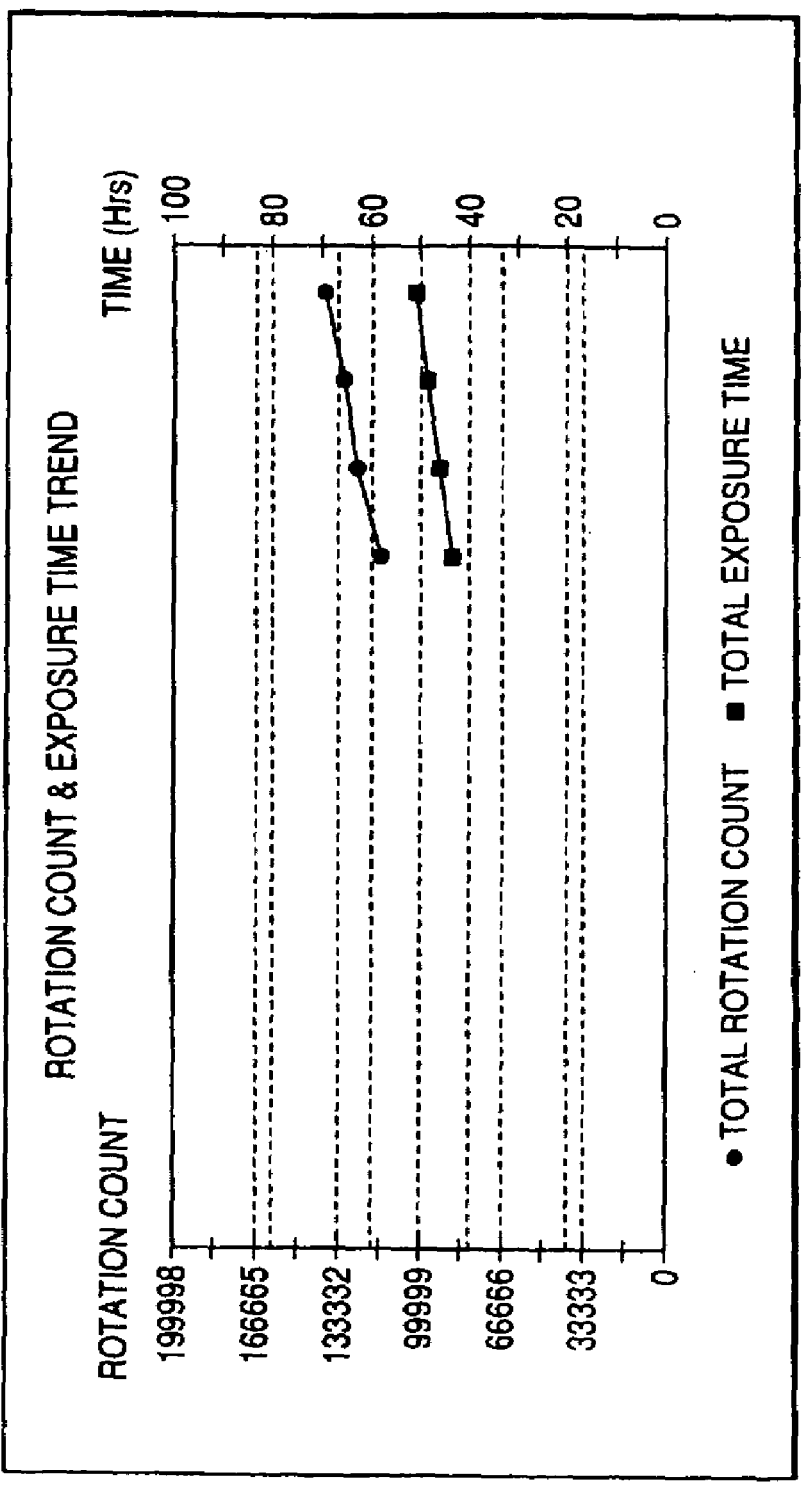
FIG. 12 is a graph of an example of tube utilization in the report according to the second embodiment.

FIG. 12 is a graph of tube utilization of an X-ray CT scanner, expressing the utilization by the number of exposures and a total tube operating time.

(Third Embodiment)

Figure 13:
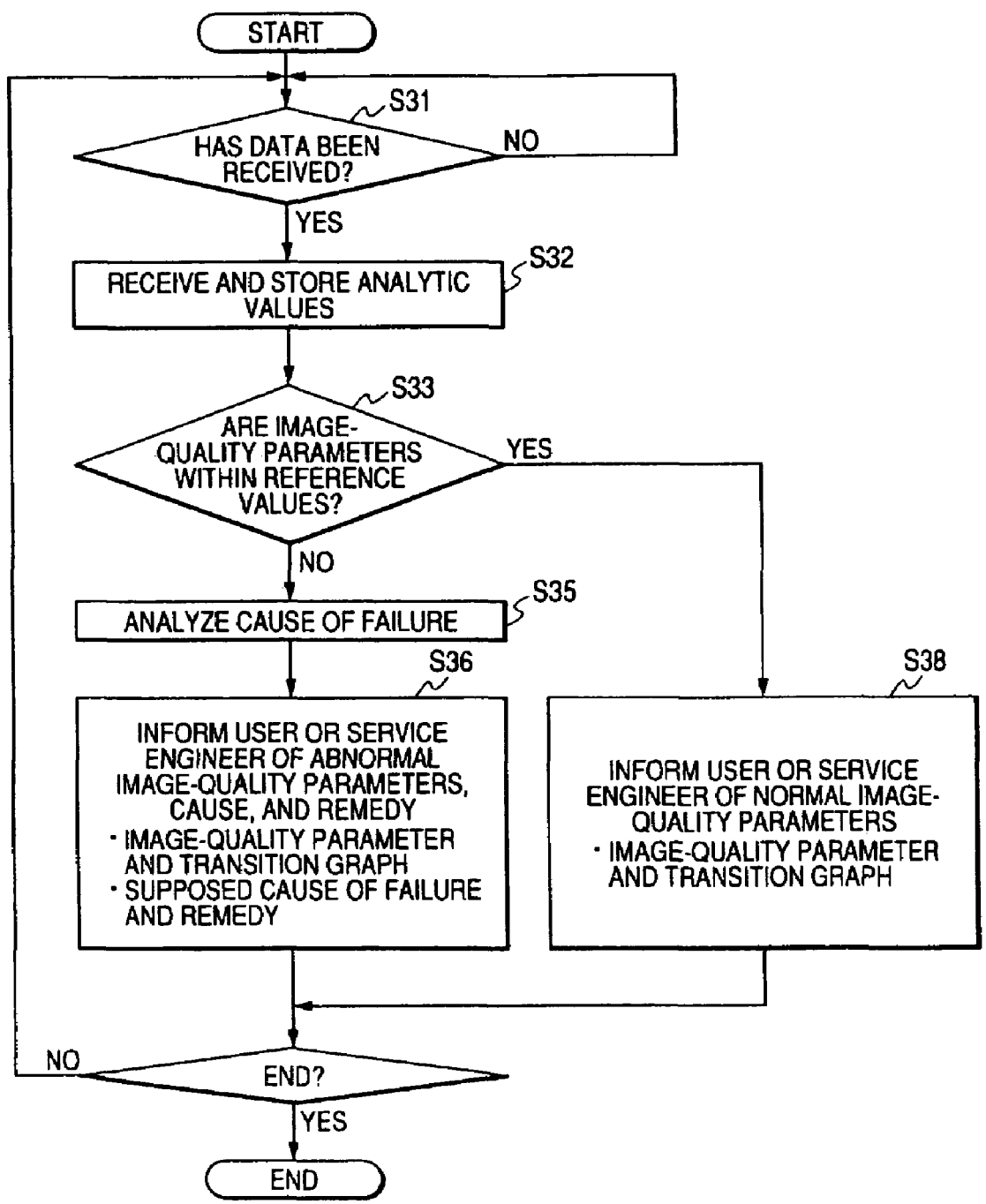
FIG. 13 is a main flowchart of a third embodiment of the invention.

An image-quality control system according to a third embodiment of the present invention will be described hereinbelow with reference to the drawings. As shown in FIG. 13, the image-quality control system of the third embodiment essentially differs from the first embodiment in that, in the flow of the image-quality control system, step S33 of determining whether or not the data of the image-quality parameters is within the image-quality-parameter reference values is followed by step S35, and the other structures and operations are substantially the same as the first embodiment and so their description will be omitted, with the same reference numerals being given.

When it is determined in step S33 that the transmitted and recorded image-quality parameters are beyond the reference values, a defect is suspected in the medical imaging equipment 21, so that the program proceeds to step S35, wherein a query for the state of degradation in image quality is sent to a cause analysis database in the apparatus-quality management database 15 to analyze the cause.

In step S36, a mail indicative of the fact that trouble occurs in the image-quality performance of the medical imaging equipment 21 and so the medical imaging equipment 21 is in failure, and supposed cause of the trouble and its remedy are transmitted to the manager of the medical imaging equipment 21 of the medical institution. Alternatively, an instruction to display a message to the same effect and that the medical imaging equipment 21 is unavailable and so an appropriate remedy is needed at the next activation of the medical imaging equipment is given to the medical imaging equipment 21 via the telecommunication units 18 and 24 through the public telecommunication network 30 to inform the user of the medical imaging equipment 21 of the fact that the equipment 21 is unavailable. Also data on the analysis of the cause of the trouble of the medical imaging equipment 21 is reported to a service engineer who maintains the medical imaging equipment 21 or a service station in charge, where information of the cause-analysis database, an operation manual for the remedy of the trouble in a remedy database, and replacement parts is presented.

Figure 14:
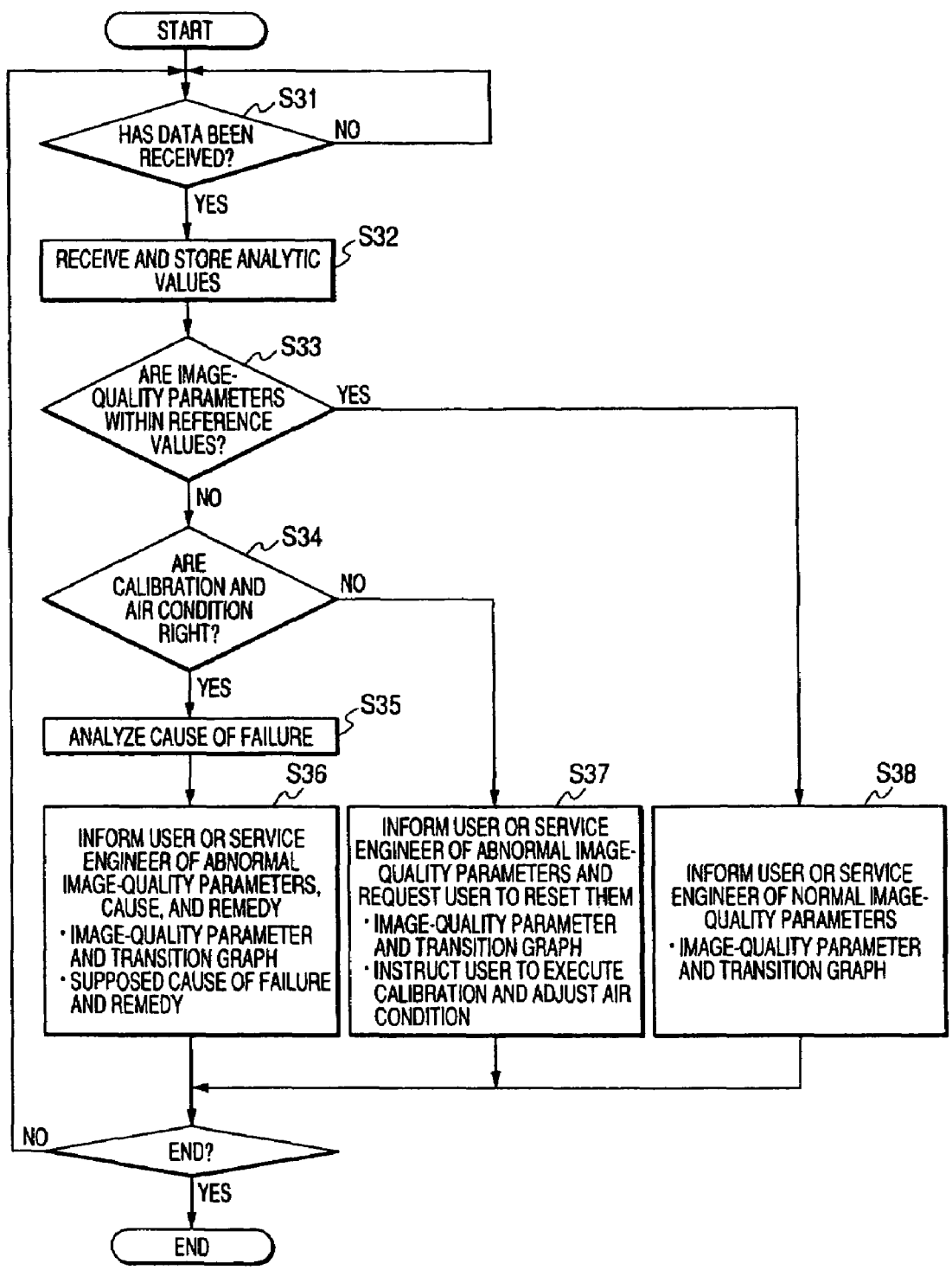
FIG. 14 is a main flowchart of a modification of the third embodiment.

A modification can be made, as shown in FIG. 14, in which the system flow according to the second embodiment and the system flow according to the third embodiment are combined.

According to the embodiments, as has been described, degradation in image quality can be determined with reference to an apparatus-quality management database, and a reference value database and a cause analysis database, which are stored in the failure-history management database 14, wherein when it is determined that the image quality is degraded, its remedy can be presented to the serviceman and the user. The apparatus-quality management database stores image-quality parameter data indicative of the image-quality performance of object medical imaging equipment and apparatus-state data indicative of a tube operating state and an environment state which are collected at the shipment and at regular intervals after installation. The reference value database stores reference values for each of corresponding body parts of the medical imaging equipment. The cause analysis database includes cause analysis information for each of defects in image quality.

Accordingly, the image-quality control system according to the embodiments has an advantage in that a failure in image quality can be recovered in a short time by searching a cause analysis database for the cause of the degradation in image quality. The system also has the advantage of preventing degradation in image quality by grasping changes in the state of the apparatus and the state of environment which lead to the degradation in image quality, since it monitors the operating state of the medical imaging equipment. The system also has the advantage of recovering degradation in image quality in a shorted time, since operating conditions and environmental conditions of the equipment, which may cause degradation in image quality, can be changed by the users themselves, such as doctors and inspecting engineers, by executing a predetermined scan plan by the users.

What is claimed is:

1. An image-quality control system comprising:
 a terminal connected to a medical diagnostic imaging apparatus; and a service center system for transmitting a maintenance report of the medical diagnostic imaging apparatus to the terminal via a network, wherein the terminal comprises:
a first receiving unit configured to receive a report transmitted from a second transmitting unit of the service center system; and
a first transmitting unit configured to transmit an image imaged by the medical diagnostic imaging apparatus or image-quality parameters of the image via the network, and
the service center system comprises:
a second receiving unit configured to receive the image or image-quality parameters transmitted from the first transmitting unit of the terminal;
an image-quality parameter database configured to store the image-quality parameters of the medical diagnostic imaging apparatus from the image or the image-quality parameters received by the second receiving unit;
a determination section configured to determine whether or not the image-quality parameters stored in the image-quality parameter database lie within specified reference values;
a report generating section configured to generate a report including the determination of the image-quality parameters by the determination section; and
a second transmitting unit configured to transmit the report including the determination of the image-quality parameters generated by the report generating section to the first receiving unit of the terminal via the network.

2. The image-quality control system according to claim 1, wherein the image-quality parameters include resolution, contrast, and linearity.

3. The image-quality control system according to claim 1, wherein
the medical diagnostic imaging apparatus is an X-ray CT scanner; and
the report generating section generates a report on CT linearity, low contrast, spatial resolution (MTF), noise, slice thickness, and uniformity of a desired phantom, as image-quality parameter information.

4. The image-quality control system according to claim 1, wherein
the service center system further comprises an environment information database storing environment information of the medical diagnostic imaging apparatus collected via the network; and
the report generating section generates a report including the determination for the image-quality parameters and the environment information.

5. The image-quality control system according to claim 1, wherein
the service center system further comprises an apparatus-operation information database storing operating information of the medical diagnostic imaging apparatus collected via the network; and
the report generating section generates a report including the determination for the image-quality parameters and information on a calibration of the medical diagnostic imaging apparatus.

6. The image-quality control system according to claim 3, wherein
the service center system further comprises an apparatus-operation information database storing operating information of the medical diagnostic imaging apparatus collected via the network; and
the report generating section generates a report of information on a latest calibration stored in the apparatus-operation information database, a temperature and humidity of an exposure room, and tube usage, in addition to CT linearity, low contrast, spatial resolution (MTF), noise, slice thickness, and uniformity of a desired phantom.

7. The image-quality control system according to claim 6, wherein the information on the latest calibration includes tube voltage and tube current to an X-ray tube, scanning time, a date and time of collecting combinations of FOVs, and wherein the information on tube usage includes X-ray-tube exposure time and rotation count.

8. The image-quality control system according to claim 1, wherein the report generating section displays a comparison of the latest information and past information to allow recognition of changes in the image-quality parameters with time.

9. The image-quality control system according to claim 4, wherein when the image-quality parameters are determined to be beyond a range of reference values, the determination section analyzes whether or not the determination that the image-quality parameters are beyond the range of the reference values is caused by the environment of the exposure room or by trouble of parts and specifies a failure part by determining normal/abnormal of at least one of the environment information of the exposure room and calibration information stored in the apparatus-operation information database.

10. The image-quality control system according to claim 1, wherein the image-quality parameters are image-quality parameters obtained when the medical diagnostic imaging apparatus imaged a phantom.

11. The image-quality control system according to claim 1, wherein when it is determined by the determination section that the image-quality parameters are beyond a range of the reference values, the second transmitting unit transmits an effect to at least one of the terminal, the medical diagnostic imaging apparatus, and a terminal owned by a service engineer.

12. The image-quality control system according to claim 1, wherein when it is determined by the determination section that the image-quality parameters are beyond the range of the reference values, at least one of a failure analyzing procedure for the medical diagnostic imaging apparatus, replacement parts for recovering the failure, and a recovery procedure for recovering the failure is determined from the determination.

* * * * *